US012622851B2

(12) United States Patent
Kawakami et al.

(10) Patent No.: US 12,622,851 B2
(45) Date of Patent: May 12, 2026

(54) HAIR TREATMENT COMPOSITION

(71) Applicant: L'OREAL, Paris (FR)

(72) Inventors: Kazumitsu Kawakami, Westfield, NJ (US); Liliana Xavier, Elizabeth, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/051,124

(22) Filed: Oct. 31, 2022

(65) Prior Publication Data

US 2024/0156699 A1 May 16, 2024

(51) Int. Cl.

| | |
|---|---|
| ***A61K 8/34*** | (2006.01) |
| ***A61K 8/25*** | (2006.01) |
| ***A61K 8/362*** | (2006.01) |
| ***A61K 8/898*** | (2006.01) |
| ***A61K 8/92*** | (2006.01) |
| ***A61Q 5/00*** | (2006.01) |
| ***A61Q 5/06*** | (2006.01) |

(52) U.S. Cl.

CPC ................ *A61K 8/342* (2013.01); *A61K 8/25* (2013.01); *A61K 8/362* (2013.01); *A61K 8/898* (2013.01); *A61K 8/92* (2013.01); *A61Q 5/002* (2013.01); *A61Q 5/06* (2013.01)

(58) Field of Classification Search

None

See application file for complete search history.

(56) References Cited

U.S. PATENT DOCUMENTS

| | | | | |
|---|---|---|---|---|
| 7,901,464 | B2 | 3/2011 | Hercouet et al. | |
| 7,927,383 | B2 | 4/2011 | Hercouet et al. | |
| 8,440,174 | B2 | 5/2013 | Panandiker et al. | |
| 8,920,787 | B2 | 12/2014 | Li et al. | |
| 8,936,798 | B2 | 1/2015 | Kitko et al. | |
| 9,072,915 | B2 * | 7/2015 | Desenne .................. | A61Q 5/00 |
| 9,221,028 | B2 | 12/2015 | Dihora et al. | |
| 9,289,630 | B2 | 3/2016 | Lee et al. | |
| 9,861,560 | B2 | 1/2018 | Bernard et al. | |
| 11,166,886 | B2 | 11/2021 | Bernard et al. | |
| 2020/0170912 | A1 * | 6/2020 | Krohn ...................... | A61K 8/31 |

FOREIGN PATENT DOCUMENTS

| | | | | |
|---|---|---|---|---|
| CA | 2746326 | C | 8/2014 | |
| EP | 2338468 | A1 | 6/2011 | |
| EP | 2146687 | B1 | 10/2011 | |
| EP | 2830713 | B1 * | 10/2017 | ............... A61Q 5/12 |
| EP | 3643292 | A1 * | 4/2020 | ............... A61K 8/11 |
| ES | 2897949 | T3 | 3/2022 | |
| FR | 3112479 | A1 | 1/2022 | |
| WO | 2014114975 | A2 | 7/2014 | |
| WO | 2016041748 | A1 | 3/2016 | |
| WO | WO-2020243605 | A1 * | 12/2020 | ............... A61Q 5/12 |

OTHER PUBLICATIONS

Preliminary Search Report and Written Opinion issued on Jul. 28, 2023 for corresponding French Application No. FR2300382.

* cited by examiner

*Primary Examiner* — Bethany P Barham
*Assistant Examiner* — Judith Marie Kamm
(74) *Attorney, Agent, or Firm* — POLSINELLI PC

(57) ABSTRACT

Hair treatment compositions and methods for using them are described. The hair treatment compositions include: (a) one or more fatty alcohols; (b) one or more liquid alkane oils; (c) a combination of cationic surfactants comprising one or more mono-alkyl cationic surfactants and one or more di-alkyl cationic surfactants; (d) a combination of silicone oils comprising one or more non-volatile dimethicone oils and one or more non-piperidinyl amino silicones; and (e) water. The hair treatment compositions are useful for treating hair, in particular, for improving the smoothness, alignment, shine, and moisturization of hair.

23 Claims, No Drawings

HAIR TREATMENT COMPOSITION

FIELD OF THE DISCLOSURE

The present disclosure relates to hair-treatment compositions and methods for treating hair with the hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Hair can become dry or damaged for various reasons, e.g., weather exposure, poor nutrition, mechanical treatments (e.g., brushing hair), styling treatments using chemicals, dying, heat, nutrition, etc. Even cleansing products can remove hair's natural oils causing dryness, which can lead to a dull appearance and to split ends.

Chemical treatments include, for example, hair bleaching and coloring, permanents, waving products, and relaxing treatments (straightening treatments). These chemical treatments change the look of hair by changing its physical structure, which inevitably causes a certain degree of damage to the hair. Environmental factors, such as salt water, sunlight, and heat, are also known to damage hair. Damaged hair is characterized by unnatural changes to the protein structure of the individual hair strands or shafts. Damage results in split ends, dry straw-like hair, hair that is easily broken, and hair that is "frizzy" and unmanageable. Because the visible portion of hair is dead, it has no ability to regenerate itself. There are numerous over the counter and salon treatments that purport to repair damaged hair. These include conditioners, hot oil treatments, hydrolyzed proteins, vitamin formulations, and exotic fruit, leaf, or root extracts. These treatments, however, provide only limited improvement to the hair. Therefore, hair repair technologies that restore the properties of hair back to their natural level are desired.

The popularity and usage of oils for dry hair treatments has increased due to their effectiveness and simplicity. Commonly used oils include olive oil, mineral oil, avocado oil, apricot kernel oil, rice bran oil, and coconut oil. However, these treatments can leave the hair feeling greasy. In addition, the effects are not usually seen after more than several hours (e.g., 8 hours) of treatment and several treatments are usually required, making it time consuming and labor intensive.

There is still a need for providing improved manageability of hair, for example, improved hair alignment, reduced unwanted volume (especially reduced frizz), and increased shine. There is also a need to develop hair care products that can impart other benefits at the same time in addition to caring and conditioning benefits, such as styling, volume, shaping, and curl definition (for curly or wavy hair).

SUMMARY OF THE DISCLOSURE

The instant disclosure relates to hair treatment compositions and methods that provide advantageous effects to hair. For example, the hair treatment compositions improve cosmetic attributes such as softness, shine, conditioning, and healthy appearance. The hair treatment compositions include unique combinations of oils, surfactants, and silicones. The inventors found that combining these elements in particular ratios influence the compositions' ability to ultimately improve the cosmetic properties of hair. The compositions can be applied to the hair and subsequently rinsed from the hair (a rinse-off product) or can be used as a leave-on product. Regardless of whether the compositions are rinsed from the hair, treatment with the compositions provides significant and surprising improvements to the hair, especially with respect to providing hair with smoothness, alignment, shine, and moisturization.

The hair treatment compositions of the instant disclosure typically include:

(a) one or more fatty alcohols;

(b) one or more liquid alkane oils;

wherein the one or more fatty alcohols of (a) and the one or more liquid alkane oils of (b) are in a weight ratio of about 20:1 to about 1:1 ((a):(b));

(c) a combination of cationic surfactants comprising or consisting of:

(c)(i) one or more mono-alkyl cationic surfactants; and (c)(ii) one or more di-alkyl cationic surfactants;

wherein the one or more mono-alkyl cationic surfactants of (c)(i) and the one or more di-alkyl cationic surfactant of (c)(ii) are in a weight ratio of about 10:1 to about 1:1 ((c)(i):(c)(ii));

(d) a combination of silicone oils comprising:

(d)(i) one or more non-volatile dimethicone oils; and (d)(ii) one or more non-piperidinyl amino silicones; and (e) water.

Nonlimiting examples of fatty alcohols include decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof. In various embodiments embodiment, a preferred fatty alcohol is cetearyl alcohol.

Nonlimiting examples of liquid alkane oils include liquid alkane oils are selected from liquid alkanes having a carbon chain length of C11 to C20, for example, isohexadecane, C15-19 alkane, isododecane, undecane, tridecane, and a combination thereof. In various embodiments, a preferred liquid alkane oil is C15-19 alkane.

In various embodiments, the one or more fatty alcohols of (a) and the one or more liquid alkane oils of (b) are in a weight ratio of about 20:1 to about 1:1 ((a):(b)). In further embodiments, it can be preferable for the one or more fatty alcohols of (a) to be in amount that is greater than the amount of the one or more liquid alkane oils of (b).

Nonlimiting examples of mono-alkyl cationic surfactants include mono-alkyl trimonium halide compounds. Examples of mono-alkyl trimonium halide compounds include, but are not limited to, cetrimonium chloride, steartrimonium chloride, behentrimonium chloride, cocotrimonium chloride, cocamidopropyltrimonium chloride. Preferred are cetrimonium chloride, steartrimonium chloride, behentrimonium chloride, and a combination thereof. In various embodiments, preferred mono-alkyl cationic surfactants include behentrimonium chloride, ceterimonium chloride, and a combination thereof.

Nonlimiting examples of di-alkyl cationic surfactants include mono-alkyl trimonium halide compounds. In various embodiments, a preferred di-alkyl cationic surfactant is dicetyldimonium chloride.

In various embodiments, the one or more mono-alkyl cationic surfactants of (c)(i) and the one or more di-alkyl cationic surfactant of (c)(ii) are in a weight ratio of about 10:1 to about 1:1 ((c)(i):(c)(ii)). In further embodiments, it can be preferably for the one or more mono-alkyl cationic surfactants of (c)(i) to be in an amount greater than the one or more di-alkyl cationic surfactants of (c)(ii). For example, the ratio of (c)(i) to (c)(ii) may be about 10:1 to about 2:1, about 8:1 to about 2:1, about 8:1 to about 3:1, or about 6:1 to about 3:1.

Nonlimiting examples of non-volatile dimethicone oils include dimethicone, dimethiconol, and a combination thereof. In various embodiments, in can be preferable for the hair treatment composition to include dimethicone.

Nonlimiting examples of non-piperidinyl amino silicones include amodimethicone, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-20, silicone quaternium-21, silicone quaternium-22, quaternium-80, silicone quaternium-2 panthenol succinate, silicone quaternium-16/glycidyl dimethicone crosspolymer, and a combination thereof. In various embodiments, it can be preferable for the hair treatment composition to include amodimethicone.

The hair treatment compositions include water, i.e., the hair treatment compositions may be considered "aqueous compositions," preferably in the form of an emulsion, and preferably an oil-in-water emulsion. In various embodiments, water constitutes at least 50 wt. % of the hair treatment composition. In further embodiments, water constitutes at least 60 wt. %, 65 wt. %, or 70 wt. % of the hair treatment composition.

In various embodiments, the hair treatment compositions include one or more water soluble organic solvents. Nonlimiting examples include glycerin, $C_2$-$C_6$ mono-alcohols, polyols (polyhydric alcohols), glycols, and a mixture thereof. In further embodiments, it can be preferable for the hair treatment composition to include glycerin, a $C_2$-$C_6$ mono-alcohol (e.g., ethanol, isopropanol, butanol, etc.), or a combination thereof.

In various embodiments, the hair treatment compositions include one or more thickening agents. Nonlimiting examples of thickening agents include polyacrylate crosspolymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a combination thereof. In various embodiments, it can be preferable for the hair treatment compositions to include one or more polysaccharides, gum, or a combination thereof, for example, hydroxypropyl guar.

In various embodiments, the hair treatment compositions include one or more C1-C9 non-polymeric and non-thiol, mono-, di-, and/or tri-carboxylic acids, and/or salts thereof. Nonlimiting examples include formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a combination thereof. In various embodiments, it can be preferable for the hair treatment composition to include citric acid, a salt thereof (e.g., sodium citrate), or a combination thereof.

In various embodiments, the hair treatment compositions include one or more emollients. Nonlimiting examples include waxes, fatty esters, and a combination thereof, for example, carnauba wax, beeswax, candelilla wax, paraffin, Japan wax, microcrystalline wax, isopropyl palmitate, isopropyl myristate, myristyl lactate, cetyl esters, isotridecyl isononanoate, C12-15 alkyl benzoate, caprylic/capric triglyceride and pentaerythrityl tetraisostearate, and a combination thereof. In various embodiments, it can be preferable for the hair treatment composition to include cetyl esters.

In various embodiments, the hair treatment composition includes one or more surfactants other than the one or more mono-alkyl cationic surfactants of (c)(i) and the one or more di-alkyl cationic surfactants of (c)(ii), i.e., "additional surfactants." Additional surfactants include nonionic surfactants, anionic surfactants, amphoteric (zwitterionic) surfactants, and cationic surfactants other than the one or more mono-alkyl cationic surfactants of (c)(i) and the one or more di-alkyl cationic surfactants of (c)(ii). In one embodiment, the hair treatment compositions include one or more nonionic surfactants. In one embodiment, the hair treatment composition includes one or more amphoteric surfactants. In one embodiment, the hair treatment composition is free or essentially free from anionic surfactants. Nonetheless, in one embodiment, the hair treatment composition includes one or more anionic surfactants.

In various embodiments, the hair treatment composition includes one or more miscellaneous ingredients. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, etc.

The hair treatment compositions of the instant disclosure are particularly useful as a rinse-off product, i.e., a product that is applied to the hair and temporarily allowed to remain on the hair, for example, massaged into the hair, and subsequently rinsed from the hair prior to styling the hair. Thus, the instant disclosure relates to methods for treating the hair with the hair treatment compositions. The methods include applying a hair treatment composition to the hair and subsequently rinsing the hair treatment composition from the hair. The hair treatment compositions may be used as a conditioner composition that is applied to the hair before or after shampooing the hair; or it can be used as a conditioner composition that used without shampooing the hair.

Typically, the hair treatment composition is applied to wet or damp hair, massaged into/throughout the hair, and subsequently rinsed from the hair before optionally drying and/or styling the hair. The hair treatment composition may be allowed to remain on the hair prior to rinsing for a period of time, for example, a period of time of about 10 seconds to about 10 minutes, prior to rinsing from the hair. The hair treatment composition may be allowed to remain on the hair prior to rinsing for a period of time of at least 5 minutes, for example, at least 5 minutes to about 15 minutes.

In certain embodiments, the hair treatment compositions of the instant disclosure may be used as a leave-on product, i.e., a product that is applied to the hair prior to and/or while styling the hair and remains on the hair after the hair is styled. The leave-on product can be applied to wet, damp, or dry hair after shampooing and optionally conditioning the hair. The leave-on product may also be applied to wet, damp, or dry hair independent of shampooing and/or conditioning.

In certain embodiments, the hair treatment compositions of the instant disclosure are particularly useful in conjunction with chemical hair treatments. For example, the hair treatment compositions can be applied to chemically treated hair as a rinse-off or leave-on product. Also, the hair treatment compositions can be used as a pre-treatment or post-treatment before or after chemically treating hair, i.e., before or after treating the hair with chemically reactive products such as oxidative hair coloring/lightening compositions and hair relaxer and/or straightening compositions.

The methods of treating hair, according to the procedures discussed above, are useful for conditioning the hair. The procedures are also useful in methods for improving natural look and feel of the hair, reducing hair frizz, improving hair smoothness, hair alignment, hair shine, and/or imparting moisturization to the hair. The methods also relate to increasing the hydrophobicity of the hair.

The hair treatment compositions disclosed herein may be provided in a kit. For example, one or more of the hair treatment compositions of the instant disclosure may be included in a kit that also include one or more additional hair treatment compositions, for example, one or more cleansing compositions, in particular, one or more shampoo compositions. Each of the one or more hair treatment compositions in the kit are separately contained. In some instances, the kits include one or more hair treatment compositions according to the instant disclosure and one or more shampoo compositions, wherein each of the one or more hair treatment compositions and the one or more shampoo compositions are separately contained.

It is to be understood that both the foregoing general description and the following detailed description are exemplary and explanatory only and are not restrictive of the disclosure. Other subjects, characteristics, aspects, and advantages of embodiments of the disclosure will emerge even more clearly on reading the description and the various examples that follow.

DETAILED DESCRIPTION OF THE DISCLOSURE

The instant disclosure relates to hair-treatment compositions and to methods for treating hair using the hair-treatment compositions. The hair-treatment compositions typically include:

(a) about 1 to about 15 wt. % of one or more fatty alcohols;

(b) one or more liquid alkane oils;

wherein the one or more fatty alcohols of (a) and the one or more liquid alkane oils of (b) are in a weight ratio of about 20:1 to about 1:1 ((a):(b));

(c) about 1 to about 10 wt. % of a combination of cationic surfactants comprising or consisting of:

(c)(i) one or more mono-alkyl cationic surfactants; and (c)(ii) one or more di-alkyl cationic surfactants;

wherein the one or more mono-alkyl cationic surfactants of (c)(i) and the one or more di-alkyl cationic surfactant of (c)(ii) are in a weight ratio of about 10:1 to about 1:1 ((c)(i):(c)(ii));

(d) about 1 to about 10 wt. % of a combination of silicone oils comprising:

(d)(i) one or more non-volatile dimethicone oils; and (d)(ii) one or more non-piperidinyl amino silicones; and (e) water;

wherein all weight percentages are based on a total weight of the hair treatment composition.

(a) Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

The fatty alcohols may be liquid or solid. In some instances, it is preferable that the hair treatment compositions include at least one solid fatty alcohol. The solid fatty alcohols that may be used include those that are solid at ambient temperature and at atmospheric pressure (25° C., 780 mmHg), and are insoluble in water, that is to say they have a water solubility of less than 1% by weight, preferably less than 0.5% by weight, at 25° C., 1 atm.

The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

Non-limiting examples of useful fatty alcohols include lauryl alcohol or lauryl alcohol (1-dodecanol); myristic or myristyl alcohol (1-tetradecanol); cetyl alcohol (1-hexadecanol); stearyl alcohol (1-octadecanol); arachidyl alcohol (1-eicosanol); behenyl alcohol (1-docosanol); lignoceryl alcohol (1-tetracosanol); ceryl alcohol (1-hexacosanol); montanyl alcohol (1-octacosanol); myricylic alcohol (1-triacontanol), and mixtures thereof.

Preferably, the solid fatty alcohol is chosen from cetyl alcohol, stearyl alcohol, behenyl alcohol and mixtures thereof such as cetylstearyl or cetearyl alcohol.

The liquid fatty alcohols, in particular those containing C10-C34, preferably have branched carbon chains and/or have one or more, preferably 1 to 3 double bonds. They are preferably branched and/or unsaturated (C═C double bond) and contain from 12 to 40 carbon atoms.

The liquid fatty alcohols may be represented by: R—OH, wherein R denotes a C12-C24 branched alkyl group or an alkenyl group (comprising at least one C12-C24 double bond C═C), R being optionally substituted by a or more hydroxy groups. Preferably, the liquid fatty alcohol is a branched saturated alcohol. Preferably, R does not contain a hydroxyl group. These include oleic alcohol, linoleic alcohol, linolenic alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and mixtures thereof. Preferably, the liquid fatty alcohol is 2-octyl-1-dodecanol.

In some instances, the hair treatment compositions include one or more fatty alcohols selected from decyl alcohol, undecyl alcohol, dodecyl, myristyl, cetyl alcohol, stearyl alcohol, cetearyl alcohol, isostearyl alcohol, isocetyl alcohol, behenyl alcohol, linalool, oleyl alcohol, myricyl alcohol and a mixture thereof. In some instances, the hair cosmetic compositions preferably include cetearyl alcohol.

The one or more fatty alcohols in the hair treatment composition may be the predominant ingredient, other than water. In other words, the hair treatment composition may include a higher total amount of the one or more fatty alcohols than any other ingredient, or class of ingredients. Accordingly, the hair treatment composition may include a higher total amount of the one or more fatty alcohols (a) than the one or more liquid alkane oils of (b); a higher total amount of the one or more fatty alcohols (a) than the combination of cationic surfactants of (c); a higher total amount of the one or more fatty alcohols (a) than the one or more mono-alkyl cationic surfactants of (c)(i); a higher total amount of the one or more fatty alcohols (a) than the one or more di-alkyl cationic surfactants of (c)(ii); a higher total amount of the one or more fatty alcohols (a) than the combination of silicone oils of (d); a higher total amount of the one or more fatty alcohols (a) than the one or more non-volatile dimethicone oils of (d)(i); a higher total amount of the one or more fatty alcohols (a) than the one or more non-piperidinyl amino silicones of (d)(ii); a higher total amount of the one or more fatty alcohols (a) than the one or more water-soluble organic solvents of (f); a higher total amount of the one or more fatty alcohols (a) than the one or more thickening agents of (g); a higher total amount of the one or more fatty alcohols (a) than the one or more C1-C9 non-polymeric and non-thiol, mono-, di-, and/or tri-carboxylic acids, salts thereof, or a combination thereof, of (h); a higher total amount of the one or more fatty alcohols (a) than the one or more emollients of (i); a higher total amount of the one or more fatty alcohols (a) than the one or more surfactants of (j); and/or a higher total amount of the one or more fatty alcohols (a) than the one or more miscellaneous ingredients of (k).

The total amount of the one or more fatty alcohols in the hair treatment composition will vary. Nonetheless, in various embodiments, the hair treatment composition includes about 1 to about 15 wt. % of the one or more fatty alcohols, based on the total weight of the hair treatment composition. In further embodiments, the hair treatment composition includes about 1 to about 12 wt. %, about 1 to about 10 wt. %, about 1 to about 8 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, about 3 to about 8 wt. %, or about 4 to about 6 wt. % of the one or more fatty alcohols, based on the total weight of the hair treatment composition.

(b) Liquid Alkane Oils

The liquid alkane oils can be volatile or non-volatile. Nonlimiting examples of liquid alkane oils include hydrocarbon oils having from 8 to 16 carbon atoms, in particular from 9 to 13 carbon atoms, and their mixtures, in particular branched $C_8$-$C_{16}$ alkanes, such as $C_8$-$C_{16}$ isoalkanes (also known as isoparaffins), such as, in particular, isododecane, isodecane or isohexadecane, and for example the oils sold under the ISOPAR™ or PERMETHYL™ trade names, and their mixtures. Preferably, the liquid alkane oil is chosen from $C_8$-$C_{16}$ isoalkanes, in particular isododecane, isodecane or isohexadecane, volatile linear $C_8$-$C_{16}$ alkanes, and their mixtures. In various embodiments, the liquid alkane oils is a volatile hydrocarbon having from 9 to 13 carbon atoms. Mention may in particular be made, as volatile $C_8$ to $C_{16}$ hydrocarbons, of linear or branched alkanes, in particular branched alkanes, such as $C_8$-$C_{16}$ isoalkanes (also known as isoparaffins), isododecane, isodecane or isohexadecane, and for example the oils sold under the ISOPAR™ or PERMETHYL™ trade names, and their mixtures. In one embodiment, the liquid alkane oil is selected from a volatile hydrocarbon solvent having from 8 to 16 carbon atoms is chosen from isododecane, isodecane, isohexadecane and their mixtures. According to a specific embodiment, the volatile solvent is isododecane. According to one embodiment, the one or more liquid alkane oils can be volatile linear alkanes comprising from 8 to 16 carbon atoms, in particular from 10 to 15 carbon atoms and more particularly from 11 to 13 carbon atoms. A volatile linear alkane suitable for the invention can advantageously be of vegetable origin. Such an alkane can be obtained, directly or in several stages, from a vegetable starting material, such as an oil, a butter, a wax, and the like.

Mention may be made, as examples of linear alkane suitable as the liquid alkane oil, of n-nonane (C9), n-decane (C10), n-undecane (C11), n-dodecane (C12), n-tridecane (C13), n-tetradecane (C14), n-pentadecane (C15), n-hexadecane (C16) and n-heptadecane (C17), and their mixtures, in particular the mixture of n-undecane (C11) and of n-tridecane (C13) sold under the reference of CETIOL™ UT by Cognis. According to a specific embodiment, a volatile linear alkane suitable for the invention can be chosen from n-nonane, n-undecane, n-dodecane, n-tridecane, n-heptadecane and their mixtures.

In various embodiments, the one or more liquid alkane oils are selected from non-volatile alkanes comprising from 10 to 30 carbon atoms, in particular from 12 to 26 carbon atoms, and more particularly from 15 to 19 carbon atoms. In one embodiment, the one or more liquid alkane oils include one or more of decane, heptane, dodecane, isododecane, isohexadecane, cyclohexane, isodecane, undecane, tridecane and mixtures thereof.

Nonlimiting examples of volatile linear alkane oils include those having an evaporation rate ranging from 0.01 to 3.5 mg/cm2/min, at room temperature (25° C.) and atmospheric pressure (760 mmHg), and comprise from 9 to 14 carbon atoms. By way of example, mention may be made of n-nonane (C9), n-decane (C10), n-undecane (C11), n-dodecane (C12), n-tridecane (C13) and n-tetradecane (C14), and mixtures thereof. In various embodiments, at least one of the one or more hydrocarbon-based oils is a hydrocarbon based oil selected from C9-C12 alkane, C10-C13 alkane, alkane, C12-C17 alkane, C13-C15 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C12-C20 isoalkane, C13-C14 isoalkane, C13-C16 isoalkane, C14-C16 isoalkane, C15-C19 isoalkane, isododecane, diethylhexylcyclohexane, undecane, tridecane, tetradecane, pentadecane, hexadecane, octadecane, docosane, squalane, hydrogenated polyisobutene, polybutene, hydrogenated polydecene, hydrogenated didecene, mineral oil, liquidum, petrolatum, dodecane, isohexadecane, isododecane, isoeicosane, and combinations thereof. In a preferred embodiment, at least one of the one or more liquid alkane oils is isododecane, C9-C16 isoalkane, C15-C19 alkane, or a combination thereof.

In a preferred embodiment, the hair treatment composition includes a mixture of alkanes of 15 to 19 carbon atoms, i.e., C15-C19 alkane.

The total amount of the one or more liquid alkane oils in the hair treatment composition will vary. Nonetheless, in various embodiments, the hair treatment composition includes about 0.1 to about 10 wt. % of the one or more liquid alkane oils. In further embodiments, the hair treatment compositions include about 0.1 to about 8 wt. %, about 0.1 to about 6 wt. %, about 0.1 to about 5 wt. %, about 0.2 to about 10 wt. %, about 0.2 to about 8 wt. %, about 0.2 to about 6 wt. %, about 0.2 to about 3 wt. %, about 0.3 to about 10 wt. %, about 0.3 to about 8 wt. %, about 0.3 to about 6 wt. %, about 0.3 to about 5 wt. % of the one or more liquid alkane oils, based on the total weight of the hair treatment composition. In yet further embodiments, the hair treatment composition includes about 0.5 to about 10 wt. %, about 1 to about 10 wt. %, about 2 to about 10 wt. %, about 3 to about 10 wt. %, about 0.5 to about 8 wt. %, about 1 to about 8 wt. %, about 2 to about 8 wt. %, or about 3 to about 8 wt. %, based on the total weight of the hair treatment composition.

The total amount of the one or more liquid alkane oils in the hair treatment composition will vary. Nonetheless, in various embodiments, the hair treatment composition includes about 0.1 to about 10 wt. % of the one or more liquid alkane oils. In further embodiments, the hair treatment compositions include about 0.1 to about 8 wt. %, about 0.1 to about 6 wt. %, about 0.1 to about 5 wt. %, about 0.2 to about 10 wt. %, about 0.2 to about 8 wt. %, about 0.2 to about 6 wt. %, about 0.2 to about 3 wt. %, about 0.3 to about 10 wt. %, about 0.3 to about 8 wt. %, about 0.3 to about 6 wt. %, about 0.3 to about 5 wt. % of the one or more liquid alkane oils, based on the total weight of the hair treatment composition. In yet further embodiments, the hair treatment composition includes about 0.5 to about 10 wt. %, about 1 to about 10 wt. %, about 2 to about 10 wt. %, about 3 to about 10 wt. %, about 0.5 to about 8 wt. %, about 1 to about 8 wt. %, about 2 to about 8 wt. %, or about 3 to about 8 wt. %, based on the total weight of the hair treatment composition.

Ratio of (a) to (b)

As already noted, the one or more fatty alcohols of (a) and the one or more liquid alkane oils of (b) are typically in a weight ratio of about 20:1 to about 1:1 ((a):(b)). Nonetheless, in various embodiments, the ratio of (a) to (b) is about 20:1 to about 1.1:1, about 20:1 to about 1.5:1, about 20:1 to about 2:1, about 18:1 to about 1.1:1, about 18:1 to about 1.5:1, about 18:1 to about 2:1, about 15:1 to about 1.1:1, about 15:1 to about 1.5:1, about 15:1 to about 2:1, about 10:1 to about 1.1:1, about 10:1 to about 1.5:1, about 10:1 to about 2:1, about 6:1 to about 1.1:1, about 6:1 to about 1.2:1, about 6:1 to about 1.5:1, or about 6:1 to about 2:1.

(c) Cationic Surfactants

The term "cationic surfactant" as defined by the instant disclosure is a surfactant that may be positively charged when it is contained in the hair treatment compositions according to the disclosure. The cationic surfactant may bear one or more positive permanent charges or may contain one or more functional groups that are cationizable in the composition according to the disclosure.

The total amount of the combination of cationic surfactants will vary. Nonetheless, in various embodiments, the hair treatment composition includes about 1 to about 12 wt. % of the combination of cationic surfactants. In further embodiments, the hair treatment composition includes about 1 to about 10 wt. %, about 1 to about 8 wt. %, about 1 to about 6 wt. %, about 2 to about 12 wt. %, about 2 to about 10 wt. %, about 2 to about 8 wt. %, about 2 to about 6 wt. %, about 3 to about 12 wt. %, about 3 to about 10 wt. %, about 3 to about 8 wt. %, or about 3 to about 6 of the combination of cationic surfactants based on the total weight of the hair treatment composition.

(c)(i) Mono-Alkyl Cationic Surfactants

Mono-alkyl cationic surfactants useful herein are primary, secondary, and tertiary amines having one long alkyl or alkenyl group of from about 12 to about 30 carbon atoms, preferably from 16 to 24 carbon atoms, more preferably from 18 to 22 alkyl group. For example, mono-alkyl cationic surfactants include mono-alkyl trimonium halide compounds. Nonlimiting examples of mono-alkyl trimonium halide compounds include cetrimonium chloride, steartrimonium chloride, behentrimonium chloride, cocotrimonium chloride, cocamidopropyltrimonium chloride. Preferred are cetrimonium chloride, steartrimonium chloride and behentrimonium chloride.

In various embodiments, the hair treatment compositions includes behentrimonium chloride, cetrimonium chloride, or a combination thereof.

Mono-alkyl cationic surfactants also include mono-alkyl amidoamines. Particularly useful are tertiary amidoamines having an alkyl group of from about 12 to about 22 carbon atoms, preferably from about 16 to about 22 carbon atoms. Exemplary tertiary amido amines include: stearamidopropyldimethylamine, stearamidopropyl-diethylamine, stearamidoethyldiethylamine, stearamidoethyldimethylamine, palmitamidopropyldimethylamine, palmitamidopropyldiethylamine, palmitamidoethyl-diethylamine, palmitamidoethyldimethylamine, behenamidopropyldimethylamine, behenamidopropyldiethylamine, behenamidoethyldiethylamine, behenamidoethyl-dimethylamine, arachidamidopropyldimethylamine, arachidamidopropyldiethylamine, arachidamidoethyldiethylamine, arachidamidoethyldimethylamine, diethylaminoethyl-stearamide, and a combination thereof.

The amount of the one or more mono-alkyl cationic surfactants in the hair treatment composition will vary. Nonetheless, in various embodiments, the hair treatment composition includes about 0.5 to about 10 wt. %, based on the total weight of the hair treatment composition. In further embodiments, the hair treatment composition includes about 0.5 to about 8 wt. %, about 0.5 to about 6 wt. %, about 0.5 to about 5 wt. %, about 1 to about 10 wt. %, about 1 to about 8 wt. %, about 1 to about 6 wt. %, about 1 to about 5 wt. %, about 2 to about 10 wt. %, about 2 to about 8 wt. %, about 2 to about 6 wt. %, about 2 to about 5 wt. %, about 3 to about 10 wt. %, about 3 to about 8 wt. %, about 3 to about 6 wt. %, or about 3 to about 5 wt. %, based on the total weight of the hair treatment composition.

(c)(ii) Di-Alkyl Cationic Surfactants

Di-alkyl cationic surfactants includes those of formula (I) and salts thereof:

Formula (I)

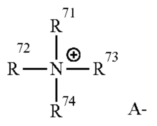

wherein two of $R^{71}$, $R^{72}$, $R^{73}$, and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms;

the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $A^-$ is an anion, for example, a halide, such as chloride or bromide, a C1-C4 alkyl sulfate such as methosulfate and ethosulfate, and mixtures thereof.

The aliphatic groups for Formula (I) can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Nonlimiting examples of di-alkyl cationic surfactants of Formula (I) include dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, dicetyldimonium chloride, dicetyldimonium bromide, and a combination thereof.

In various embodiments, the one or more di-alkyl cationic surfactants are selected from di-alkyl dimonium halide compounds. Nonlimiting examples include dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, dicetyldimonium chloride, dicetyldimonium bromide, and a combination thereof. In a preferred embodiment, the di-alkyl dimonium halide compounds are selected from dicetyldimonium chloride, dicetyldimonium bromide, and a combination thereof.

In a preferred embodiment, the hair treatment composition includes dicetyldimonium chloride.

The total amount of the one or more di-alkyl cationic surfactants in the hair treatment composition will vary. Nonetheless, in various embodiments, the hair treatment composition includes about 0.1 to about 8 wt. % of the one or more di-alkyl cationic surfactants, based on the total weight of the hair treatment composition. In further embodiments, the hair treatment composition includes about about 0.1 to about 6 wt. %, about 0.1 to about 5 wt. %, about 0.1 to about 3 wt. %, about 0.1 to about 2 wt. %, about 0.5 to about 8 wt. %, about 0.5 to about 6 wt. %, about 0.5 to about 5 wt. %, about 0.5 to about 3 wt. %, about 0.5 to about 2 wt. %, about 0.6 to about 5 wt. %, about 0.6 to about 4 wt. %, about 0.6 to about 3 wt. %, or about 0.6 to about 2 wt. % of the one or more di-alkyl cationic surfactants, based on the total weight of the hair treatment composition.

Ratio of (c)(i) to (c)(ii)

As already noted, the one or more mono-alkyl cationic surfactants of (c)(i) and the one or more di-alkyl cationic surfactant of (c)(ii) are typically in a weight ratio of about 10:1 to about 1:1 ((c)(i):(c)(ii)). Nonetheless, in various embodiments, the ratio of (c)(i) to (c)(ii) is about 10:1 to about 1.1:1, about 10:1 to about 1.5:1, about 10:1 to about 2:1, about 10:1 to about 3:1, about 10:1 to about 4:1, about 8:1 to about 1.1:1, about 8:1 to about 1.5:1, about 8:1 to about 2:1, about 8:1 to about 3:1, about 8:1 to about 4:1, about 6:1 to about 1.1:1, about 6:1 to about 1.5:1, about 6:1 to about 2:1, about 6:1 to about 3:1, or about 6:1 to about 4:1.

(d) Silicone Oils (d)(i) Non-Volatile Dimethicone Oils

The non-volatile dimethicone oil may be phenylated or non-phenylated. Preferably, the non-volatile dimethicone oil is non-phenylated. Nonlimiting examples include alkyl dimethicones, vinyl methyl methicones, and also dimethicone modified with optionally fluorinated aliphatic groups, or with functional groups such as hydroxyl, thiol and/or amine groups. The non-volatile dimethicone oil is preferably chosen from polydimethylsiloxanes and/or alkyl dimethicones, and mixture thereof. Preferably, the non-phenylated non-volatile dimethicone oils is selected from non-volatile polydimethylsiloxanes (PDMS), PDMSs comprising alkyl or alkoxy groups, which are pendent and/or at the end of the silicone chain, these groups each containing from 2 to 24 carbon atoms, such as cetyldimethicone sold under the commercial reference ABIL™ WAX 9801 from Evonik Goldschmidt, PDMSs comprising aliphatic and/or aromatic groups, polyalkylmethylsiloxanes such as cetyldimethicone, or polyalkylmethylsiloxane optionally substituted with a fluorinated group, such as polymemyltrffluoropropyldimethylsiloxanes, polyalkylmethylsiloxanes, polysiloxanes modified with fatty acids, fatty alcohols or polyoxyalkylenes, and mixtures thereof.

Preferably the non-volatile dimethicone oil is linear.

The amount of the one or more non-volatile dimethicone oils in the hair treatment compositions will vary. Nonetheless, in various embodiments, the hair treatment composition includes about 0.5 to about 20 wt. %, based on the total weight of the hair treatment composition. In further embodiments, the hair treatment composition includes about 0.5 to about 15 wt. %, about 0.5 to about 12 wt. %, about 0.5 to about 10 wt. %, about 0.5 to about 8 wt. %, about 0.5 to about 5 wt. %, about 1 to about 20 wt. %, about 1 to about 15 wt. %, about 1 to about 12 wt. %, about 1 to about 10 wt. %, about 1 to about 8 wt. %, about 1 to about 5 wt. %, about 2 to about 20 wt. %, about 2 to about 15 wt. %, about 2 to about 12 wt. %, about 2 to about 10 wt. %, about 2 to about 7 wt. %, or about 2 to about 5 wt. %, based on the total weight of the hair treatment composition.

(d)(ii) Non-Piperidinyl Amino Silicones

The term "amino silicone" is intended to indicate any silicone comprising at least one primary, secondary or tertiary amine or a quaternary ammonium group without piperidinyl groups. The term "amino silicone" is interchangeable with the term "amino-functionalized silicones." In some instances, the amino silicones are alkoxylated and/or hydroxylated amino silicones.

Nonlimiting examples of amino silicones include amodimethicone, quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof.

Further non-limiting examples of amino silicones include bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a mixture thereof.

In a preferred embodiment, the hair treatment composition includes amomdimethicone.

The amount of the one or more non-piperidinyl amino silicones in the hair treatment composition will vary. Nonetheless, in various embodiments, the hair treatment composition includes about 0.1 to about 15 wt. %, based on the total weight of the hair treatment composition. In further embodiments, the hair treatment composition includes about 0.1 to about 12 wt. %, about 0.1 to about 10 wt. %, about 0.1 to about 8 wt. %, about 0.1 to about 5 wt. %, 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 12 wt. %, about 1 to about 10 wt. %, about 1 to about 8 wt. %, about 1 to about 5 wt. %, about 1.5 to about 15 wt. %, about 1.5 to about 12 wt. %, about 1.5 to about 10 wt. %, about 1.5 to about 8 wt. %, or about 1.5 to about 5 wt. %, based on the total weight of the hair treatment composition.

(e) Water

The amount of water in the hair treatment compositions will vary. Nonetheless, in various embodiments, the hair treatment composition includes about 50 to about 92 wt. % water, based on the total weight of the hair treatment composition. In further embodiments, in further embodiments, the hair treatment composition includes about 60 to about 92 wt. %, about 65 to about 92 wt. %, about 70 to about 92 wt. %, about 75 to about 92 wt. %, about 50 to about 90 wt. %, about 60 to about 90 wt. %, about 65 to about 90 wt. %, about 70 to about 90 wt. %, about 75 to about 90 wt. %, about 50 to about 85 wt. %, about 60 to about 85 wt. %, ab out 65 to about 85 wt. %, about 70 to about 85 wt. %, about 75 to about 85 wt. %, about 50 to about 80 wt. %, about 60 to about 80 wt. %, about 65 to about 80 wt. %, about 70 to about 80 wt. %, or about 75 to about 80 wt. %, based on the total weight of the hair treatment composition.

(f) Water-Soluble Organic Solvent

The term "water-soluble organic solvent" is interchangeable with the terms "water-miscible organic solvent" or just "water-soluble solvent" and relates to organic compounds that are liquid at 25° C. and at atmospheric pressure (760 mmHg), and have a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-15}$, $C_{1-10}$, or $C_{1-4}$ alcohols), polyols (polyhydric alcohols), glycols (e.g., propylene glycol, butylene glycol, caprylyl glycol, etc.), and a mixture thereof.

Non-limiting examples of water-soluble organic solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of are ethylene glycol, propylene glycol, butylene glycol, hexylene glycol, propane diol, and glycerin. The organic solvents can be volatile or non-volatile compounds.

Further non-limiting examples of water-soluble organic solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some instances, polhydric alcohols may be particularly useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the hair treatment compositions include one or more water-soluble organic solvents chosen from chosen glycerin, $C_{1-6}$ mono-alcohols, polyols (polyhydric alcohols), glycols, and a mixture thereof. In an even more preferred embodiment, the hair treatment compositions include one or more water-soluble solvents chosen from glycerin, $C_{1-6}$ mono-alcohols, and a combination therefore, in particular, a combination of glycerin and a monoalcohol chosen from isopropanol, ethanol, and mixtures thereof.

The total amount of the one or more water-soluble organic solvents in the hair treatment composition will vary. Nonetheless, in various embodiments, the hair treatment composition includes about 0.1 to about 20 wt. % of the one or more water-soluble organic solvents, based on the total weight of the hair treatment composition. In further embodiments, the hair treatment composition includes about 0.1 to about 15 wt. %, about 0.1 to about 12 wt. %, about 0.1 to about 10 wt. %, about 0.1 to about 8 wt. %, about 0.5 to about 20 wt. %, about 0.5 to about 15 wt. %, about 0.5 to about 12 wt. %, about 0.5 to about 10 wt. %, about 0.5 to about 8 wt. %, about 1 to about 20 wt. %, about 1 to about 15 wt. %, about 1 to about 12 wt. %, about 1 to about 10 wt. %, about 1 to about 8 wt. %, about 1 to about 5 wt. %, about 2 to about 20 wt. %, about 2 to about 15 wt. %, about 2 to about 12 wt. %, about 2 to about 8 wt. %, or about 2 to about 5 wt. % of the one or more water-soluble organic solvents, based on the total weight of the hair treatment composition.

(g) Thickening Agents

As the name suggests, thickening agent influence the viscosity of the hair treatment compositions. Nonlimiting examples of useful thickening agents include carboxylic acid polymers, crosslinked polyacrylate polymers, polyacrylamide polymers, polysaccharides, gums, modified gums, and a combination thereof. In particular, the following thickening agents are illustrative:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL™, ACRYSOL™, POLYGEL™, SOKALAN™ and CARBOPOL ULTREZ™. Examples of commercially available carboxylic acid polymers include the carbomers, which are homopolymers of acrylic acid crosslinked with allyl ethers of sucrose or pentaerytritol. The carbomers are available as the CARBOPOL™ 900 series from B.F. Goodrich (e.g., CARBOPOL™ 954). In addition, other suitable carboxylic acid polymeric agents include ULTREZ™ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL™ 1342, CARBOPOL™ 1382, PEMULEN™ TR-1, and PEMULEN™ TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN™ from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT™ HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

c. Polyvinylpyrrolidone (PVP) and co-polymers: Non-limiting examples include Polyvinylpyrrolidone(PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL™ K30, K85, K90 available from BASF. Commercially available copolymers of vinylpyrrolidone and vinylacetate include LUVISKOL™ VA37, VA64 available from BASF; copolymers of vinylpyrrolidone, methacrylamide, and vinylimidazole (INCI: VP/Methacrylamide/Vinyl Imidazole Copolymer) is commercially available as LUVISET™ from BASF. In some instances, PVP and PVP/VA copolymer are preferred.

d. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

e. Polyglyceryl esters: Non-limiting polyglycerol esters of fatty acids (polygylceryl esters) include those of the following formula:

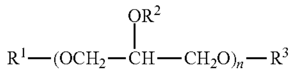

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

f. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

g. Gums, including natural gums and modified gums: nonlimiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, derivatives thereof, etc.

In various embodiments, the hair treatment compositions include one more guar gums including one or more derivatives of guar gums or modified guar gums, in particular, nonionic guar gums including one or more nonionic derivatives of guar gums or nonionic modified guar gums. For simplicity, the term "nonionic guar gum" is intended to mean modified nonionic guar gums and unmodified nonionic guar gums.

Unmodified nonionic guar gums include, for example, the products sold under the name VIDOGUM™ GH 175 by the company UNIPECTINE™ and under the names MEYPRO GUAR™ 50 and JAGUAR™ C by the company Rhodia Chimie. Modified nonionic guar gums include, for example, guar gums modified with $C_1$-$C_6$ hydroxyalkyl groups. Among the hydroxyalkyl groups that may be mentioned, for example, are hydroxymethyl, hydroxyethyl, hydroxypropyl and hydroxybutyl groups. Hydroxyalkylated guar gums can be prepared, for example, by reacting corresponding alkene oxides such as, for example, propylene oxides, with the guar gum to obtain a guar gum modified with hydroxyalkyl groups and/or hydroxypropyl groups. The degree of hydroxyalkylation, which corresponds to the number of alkylene oxide molecules consumed by the number of free hydroxyl functions present on the guar gum, preferably ranges from 0.4 to 1.2. Such nonionic guar gums optionally modified with hydroxyalkyl groups are sold, for example, under the trade names JAGUAR™ HP8, JAGUAR™ HP60 and JAGUAR™ HP120, JAGUAR™ DC 293 and JAGUAR™ HP 105 by the company Rhodia Chimie or under the name GALACTASOL™ 4H4FD2 by the company Aqualon.

Also suitable are nonionic guar gums modified with hydroxyalkyl groups, more especially hydroxypropyl groups, modified with groups comprising at least one $C_6$-$C_{30}$ fatty chain. By way of example of such compounds, mention may be made, inter alia, of products RE210-18™ ($C_{14}$ alkyl chain) and RE205-1™ ($C_{20}$ alkyl chain) sold by the company Rhodia Chimie. In various embodiments, a guar gum comprises at least one $C_6$-$C_{30}$ fatty chain.

In a preferred embodiment, the hair treatment compositions of the instant disclosure include a guar gum and/or a modified guar gum, preferably a nonionic guar gum or modified guar gum, more preferably hydroxypropyl guar.

The total amount of the one or more thickening agents in the hair treatment compositions will vary. Nonetheless, in various embodiments, the hair treatment composition includes about 0.01 to about 8 wt. %, about 0.01 to about 5 wt. %, about 0.01 to about 4 wt. %, about 0.01 to about 3 wt. %, about 0.05 to about 8 wt. %, about 0.05 to about 5 wt. %, about 0.05 to about 4 wt. %, about 0.05 to about 3 wt. %, about 0.1 to about 8 wt. %, about 0.1 to about 5 wt. %, about 0.1 to about 4 wt. %, about 0.1 to about 3 wt. %, about 0.2 to about 8 wt. %, about 0.2 to about 5 wt. %, about 0.2 to about 4 wt. %, about 0.2 to about 3 wt. %, or about 0.3 to about 3 wt. %, based on the total weight of the hair treatment composition.

(h) C1-C9 Non-Thiol Mono-, Di-, and/or Tri-Carboxylic Acids

Nonlimiting examples of C1-C9 non-polymeric and non-thiol, mono-, di-, and tri-carboxylic acids include formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a mixture thereof. In various embodiments, the hair treatment composition includes:

at least one monocarboxylic acid selected from formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, a salt thereof, and a mixture thereof;

at least one dicarboxylic acid selected from oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, a salt thereof, and a mixture thereof; and/or at least one tricarboxylic acid selected from citric acid, isocitric acid, aconitric acid, propane-1,2,3-tricarboxylic acid, and benzene-1,3,5-tricarboxylic acid, a salt thereof, and a mixture thereof.

In a preferred embodiment, the hair treatment compositions includes citric acid, a salt thereof, or a combination thereof, preferably a combination of citric acid and sodium citrate.

The total amount of the one or more one or more C1-C9 non-polymeric and non-thiol, mono-, di-, and/or tri-carboxylic acids, and/or salts thereof, in the hair treatment compositions will vary. Nonetheless, in various embodiments, the hair treatment composition includes about 0.1 to about 10 wt. % of the one or more C1-C9 non-polymeric and non-thiol, mono-, di-, and/or tri-carboxylic acids, and/or salts thereof, based on the total weight of the hair treatment composition. In further embodiments, the hair treatment composition includes about 0.1 to about 8 wt. %, about 0.1 to about 5 wt. %, about 0.1 to about 4 wt. %, about 0.5 to about 10 wt. %, about 0.5 to about 8 wt. %, about 0.5 to about 5 wt. %, about 0.5 to about 4 wt. %, about 1 to about 10 wt. %, about 1 to about 8 wt. %, about 1 to about 5 wt. %, about 1 to about 4 wt. %, about 1.5 to about 10 wt. %, about 1.5 to about 8 wt. %, about 1.5 to about 5 wt. %, about 1.5 to about 4 wt. %, about 2 to about 10 wt. %, about 2 to about 8 wt. %, about 2 to about 5 wt. %, or about 2 to about 4 wt. % of the one or more C1-C9 non-polymeric and non-thiol, mono-, di-, and/or tri-carboxylic acids, and/or salts thereof, based on the total weight of the hair treatment composition.

(i) Emollients

Emollients can provide moisturizing, sealing, and lubricating properties to the hair. Nonlimiting examples of emollients include fruit and/or vegetable-derived oils and butters, proteins and/or hydrolyzed proteins, mineral oil, petrolatum, and fatty materials that are solid at room temperature (25° C.). Many emollients are hydrophobic, but other may be hydrophilic. Hydrolyzed proteins and fruit and vegetable oils are typically smaller molecules with fatty acid components that are hydrophilic. This may enable various emollients to act as both emollients and as mild humectants. Various emollients can at least partially penetrate the cuticle layer into the cortex and significantly improve the mechanical properties of the hair.

In various embodiments, the hair treatment compositions include one or more emollients selected from waxes, fatty esters, and a combination thereof (for example carnauba wax, beeswax, candelilla wax, paraffin, Japan wax, microcrystalline wax, isopropyl palmitate, isopropyl myristate, myristyl lactate, cetyl esters, isotridecyl isononanoate, C12-15 alkyl benzoate, caprylic/capric triglyceride and pentaerythrityl tetraisostearate, and a combination thereof).

In one embodiment, emollients include various silicones other than the silicone oils of (d). However, another embodiment, the hair treatment composition is free or essentially free from silicones other than the silicone oils of (d).

In a preferred embodiment, at least one of the one or more emollients is cetyl esters.

The total amount of the one or more emollients in the hair treatment compositions will vary. Nonetheless, in various embodiments, the total amount of the one or more emollients in the hair treatment compositions is from about 0.01 to about 8 wt. %, based on the total weight of the hair treatment composition. In further embodiments, the total amount of the one or more emollients in the hair treatment composition is from about 0.01 to about 6 wt. %, about 0.01 to about 5 wt. %, about 0.01 to about 3 wt. %, about 0.05 to about 8 wt. %, about 0.05 to about 5 wt. %, about 0.05 to about 3 wt. %, about 0.1 to about 8 wt. %, about 0.1 to about 5 wt. %, about 0.1 to about 3 wt. %, about 0.5 to about 8 wt. %, about 0.5 to about 5 wt. %, or about 0.5 to about 3 wt. %, based on the total weight of the hair treatment composition.

(j) Surfactants

The hair treatment compositions of the instant disclosure may optionally include one or more surfactants other than the cationic surfactants in the combination of cationic surfactants of (d). For purposes of the instant disclosure, surfactants other than the one or more cationic surfactants in the combination of cationic surfactants of (d) may be referred to as "additional surfactants." The additional surfactants may be anionic, cationic, nonionic or amphoteric/zwitterionic. In one embodiment, the hair treatment compositions include one or more nonionic surfactants. In one embodiment, the hair treatment composition includes one or more amphoteric surfactants. In one embodiment, the hair treatment composition is free or essentially free from anionic surfactants. Nonetheless, in one embodiment, the hair treatment composition includes one or more anionic surfactants.

The total amount of the one or more additional surfactants in the hair treatment compositions will vary. Nonetheless, in various embodiments, the hair treatment composition includes about 0.01 to about 10 wt. % of the one or more additional surfactants, based on the total weight of the hair treatment composition. In further embodiments, the hair treatment composition includes about 0.01 to about 8 wt. %, about 0.01 to about 5 wt. %, about 0.01 to about 3 wt. %, about 0.05 to about 10 wt. %, about 0.05 to about 8 wt. %, about 0.05 to about 5 wt. %, about 0.05 to about 3 wt. %, about 0.1 to about 10 wt. %, about 0.1 to about 8 wt. %, about 0.1 to about 5 wt. %, or about 0.1 to about 3 wt. % of the one or more additional surfactants, based on the total weight of the hair treatment composition.

In one embodiment, the hair treatment compositions include one or more nonionic surfactants. Nonionic surfactants often provide emulsification properties to compositions. Accordingly, for purposes of the instant disclosure the term "nonionic surfactants" encompasses emulsifiers, which can be useful in formatting the hair treatment compositions as emulsions.

Nonionic Surfactants

The hair treatment compositions may optionally include one or more nonionic surfactants. Nonionic surfactants can be useful for enhancing emulsification. Therefore, nonionic surfactants may also be referred to as nonionic emulsifiers.

The nonionic surfactants include surfactants/emulsifier that are useful for forming a oil-in-water emulsion. For example, the nonionic surfactants may be chosen from alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof. In some instances, polyglycerolated C8-C30 fatty acid esters are particularly useful include those chosen from polyglycerolated esters of C12-C18 fatty acids, in particular lauric, myristic, palmitic, stearic or isostearic acid, having from 2 to 16 mol of glycerol.

Nonlimiting examples of polyglycerolated fatty acid esters include polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof. In some instances, polyglyceryl-2 isostearate is particularly useful.

The nonionic surfactants/emulsifiers may be chosen from alcohols and alpha-diols, these compounds being polyethoxylated and/or polypropoxylated and/or polyglycerolated, the number of ethylene oxide and/or propylene oxide groups possibly ranging from 2 to 100, and the number of glycerol groups possibly ranging from 2 to 30; these compounds comprising at least one fatty chain comprising from 8 to 30 carbon atoms and especially from 16 to 30 carbon atoms.

Mention is also be made of polyethoxylated fatty amides preferably having from 2 to 30 ethylene oxide units, polyglycerolated fatty amides including on average from 1 to 5, and in particular from 1.5 to 4, glycerol groups; polyoxyethylenated fatty acid esters of sorbitan having preferably from 2 to 40 units of ethylene oxide, fatty acid esters of sucrose, polyoxyalkylenated and preferably polyoxyethylenated fatty acid esters containing from 2 to 150 mol of ethylene oxide, such as oxyethylenated plant oils.

Useful nonionic surfactants include those of the alkyl (poly)glycoside type, represented especially by the following general formula: $R_1O—(R_2O)_t-(G)_v$ in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents an alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly)glycoside surfactant may be an alkyl(poly)glucoside surfactant $C_8/C_{16}$ alkyl (poly)glucosides 1,4, and in particular decyl glucosides and caprylyl/capryl glucosides.

Useful nonionic surfactants may be chosen from polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof.

The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 2 EO (Ceteth-2) (HLB 5.3) cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3) lauryl alcohol polyoxyethylenated with 2 EO (Laureth-2) (HLB 6.1) lauryl alcohol polyoxyethylenated with 3 EO (Laureth-3) (HLB 8) lauryl alcohol polyoxyethylenated with 4 EO (Laureth-4) (HLB 9.4) lauryl alcohol polyoxyethylenated with 7 EO (Laureth-7) (HLB 12.3) lauryl alcohol polyoxyethylenated with 9 EO (Laureth-9) (HLB 13.6) lauryl alcohol polyoxyethylenated with 10 EO (Laureth-10) (HLB 13.9) lauryl alcohol polyoxyethylenated with 12 EO (Laureth-12) (HLB 14.6) lauryl alcohol polyoxyethylenated with 21 EO (Laureth-21) (HLB 15.5) lauryl alcohol polyoxyethylenated with 23 EO (Laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5).

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15). In a preferred embodiment, the hair treatment compositions include one or more nonionic surfactants chosen from polyoxyethylenated C8-C30 fatty acid esters (preferably C12-C18) of sorbitan, preferably polyoxyethylenated esters of C12-C18 fatty acids.

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

In one embodiment, the hair treatment composition includes one or more ethoxylated tridecyl alcohols having 3 to 50, 3 to 25, or 3 to 20 ethylene oxide units per tridecyl group. In one embodiment, the hair treatment composition includes trideceth-6.

In one embodiment, the hair treatment composition includes one or more nonionic surfactant selected from trideceth-6, trideceth-10, PEG-100 stearate, steareth-6, trideceth-3, or a combination thereof.

In various embodiments, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids mention is made of glyceryl stearate (glyceryl mono-, di- and/or tristearate) (CTFA name: glyceryl stearate) or glyceryl ricinoleate and mixtures thereof.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL™ 165 by Uniqema, and the product containing glyceryl stearate (glyceryl mono- and distearate) and potassium stearate marketed under the name TEGIN™ by Goldschmidt (CTFA name: glyceryl stearate SE), can also be used.

Alkyl polyglucosides are a class of useful nonionic surfactants. Non-limiting examples of alkyl polyglucosides include alkyl polyglucosides having the following formula:

$$R^1—O—(R^2O)_n—Z(x)$$

wherein $R^1$ is an alkyl group having 8-18 carbon atoms;

$R^2$ is an ethylene or propylene group;

Z is a saccharide group with 5 to 6 carbon atoms;

n is an integer from 0 to 10; and x is an integer from 1 to 5.

Useful alkyl poly glucosides include lauryl glucoside, octyl glucoside, decyl glucoside, coca glucoside, sucrose laurate, caprylyl/capryl glucoside, and sodium lauryl glucose carboxylate, and mixtures thereof. Typically, the at least one alkyl poly glucoside compound is selected from the group consisting of lauryl glucoside, decyl glucoside and coca glucoside, and more typically lauryl glucoside. In some instances, decyl glucoside is particularly preferred.

In various embodiments, the hair treatment compositions include one or more nonionic surfactants. The total amount of the one or more nonionic surfactants will vary. Nonetheless, in various embodiments, the hair treatment composition includes about 0.01 to about 8 wt. % of the one or more nonionic surfactants. In further embodiments, the hair treatment composition includes about 0.01 to about 5 wt. %, about 0.01 to about 3 wt. %, about 0.05 to about 8 wt. %, about 0.05 to about 5 wt. %, about 0.05 to about 3 wt. %, about 0.1 to about 8 wt. %, about 0.1 to about 5 wt. %, or about 0.1 to about 3 wt. % of the one or more surfactants, based on the total weight of the hair treatment composition.

(k) Miscellaneous Ingredients

Miscellaneous ingredients are ingredients that are compatible with the hair treatment compositions and do not disrupt or materially affect the basic and novel properties of the compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, etc.

In various embodiments, the hair treatment compositions include one or more miscellaneous ingredients selected from preservatives, fragrances, pH adjusters, salts, chelating agents, buffers (other than the mono-, di-, and/or tri-carboxylic acids and/or salts thereof of (h)), composition colorants, and mixtures thereof. Nonlimiting examples of specific miscellaneous ingredients include phenoxyethanol (preservative), dilauryl thiodipropionate (antioxidant or sequestering agent), trisodium HEDTA (chelating agent or preservative), and a combination thereof.

In the context of the instant disclosure, a "composition colorant" is a compound that colors the composition but does not have an appreciable coloring effect on hair. In other words, the composition colorant is included to provide a coloring to the composition for aesthetic appeal, which is not intended to impart coloring properties to hair. Styling gels, for example, can be found in a variety of different colors (e.g., light blue, light pink, etc.) yet application of the styling gel to the hair does not change the color of the hair.

The total amount of the one or more miscellaneous ingredients in the hair treatment compositions will vary. Nonetheless, in various embodiments, the hair treatment composition includes about 0.01 to about 10 wt. % of the one or more miscellaneous ingredients, based on the total weight of the hair treatment composition. In further embodiments, the hair treatment composition includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt. %, or about 1 to about 3 wt. % of the one or more miscellaneous ingredients, based on the total weight of the hair treatment composition.

EMBODIMENTS

In various embodiments, the hair treatment composition comprises or consists of:

(a) about 1 to about 15 wt. %, preferably about 1 to about 10 wt. %, more preferably about 2 to about 8 wt. % of one or more fatty alcohols, preferably one or more fatty alcohols selected from cetearyl alcohol, decyl alcohol, undecyl alcohol, dodecyl alcohol, myristyl alcohol, cetyl alcohol, stearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof, more preferably one or more fatty alcohols selected from cetearyl alcohol, myristyl alcohol, cetyl alcohol, stearyl alcohol, isostearyl alcohol, isocetyl alcohol, behenyl alcohol, even more preferably cetearyl alcohol;

(b) about 0.1 to about 10 wt. %, preferably about 0.2 to about 8 wt. %, more preferably about 0.3 to about 6 wt. % of one or more liquid alkane oils, preferably one or more liquid alkanes selected from alkanes having a carbon chain length of C11 to C20, more preferably, C9-C12 alkane, C10-C13 alkane, C12-C17 alkane, C13-C15 alkane, C14-C17 alkane, C14-C19 alkane, C14-C20 alkane, C14-C22 alkane, C15-C19 alkane, C21-C28 alkane, C17-C23 alkane, C9-C12 isoalkane, C9-C13 isoalkane, C9-C14 isoalkane, C9-C16 isoalkane, C10-C11 isoalkane, C10-C12 isoalkane, C10-C13 isoalkane, isoalkane, C11-C13 isoalkane, C11-C14 isoalkane, C12-C14 isoalkane, C12-C20 isoalkane, C13-C14 isoalkane, C13-C16 isoalkane, C14-C16 isoalkane, C15-C19 isoalkane, even more preferably C15-19 alkane;

wherein the one or more fatty alcohols of (a) and the one or more liquid alkane oils of (b) are in a weight ratio of about 20:1 to about 1:1, preferably wherein the ratio of (a) to (b) is about 18:1 to about 1.1:1, more preferably wherein the ratio of (a) to (b) is about 10:1 to about 1.5:1;

(c) about 1 to about 10 wt. %, preferably about 2 to about 8 wt. %, more preferably about 3 to about 8 wt. % of a combination of cationic surfactants, based on the total amount of the hair treatment composition. of a combination of cationic surfactants comprising:

(c)(i) about 1 to about 8 wt. %, preferably about 1 to about 6 wt. %, more preferably about 2 to about 6 wt. % of one or more mono-alkyl cationic surfactants, preferably one or more mono-alkyl trimonium halide compounds, more preferably one or more mono-alkyl trimonium halide compounds selected from behentrimonium chloride, cetrimonium chloride, and a combination thereof; and (c)(ii) about 0.1 to about 6 wt. %, preferably about 0.5 to about 5 wt. %, more preferably about 0.5 to about 4 wt. % of one or more di-alkyl cationic surfactants, preferably one or more di-alkyl dimonium halide compounds, especially, dicetyldimonium chloride;

wherein the one or more mono-alkyl cationic surfactants of (c)(i) and the one or more di-alkyl cationic surfactant of (c)(ii) are in a weight ratio of about 10:1 to about 1:1 ((c)(i):(c)(ii))'

(d) about 1 to about 10 wt. %, preferably about 1 to about 8 wt. %, more preferably about 2 to about 6 wt. % of a combination of silicone oils comprising:

(d)(i) about 0.5 to about 8 wt. %, preferably about 1 to about 8 wt. %, more preferably about 2 to about 6 wt. % of one or more dimethicone oils, preferably a liner, non-phenylated dimethicone oil, more preferably selected from polydimethylsiloxanes and/or alkyl dimethicones, or a combination thereof, and most preferably dimethicone; and (d)(ii) one or more non-piperidinyl amino silicones, preferably one or more non-piperidinyl amino silicones selected from amodimethicone, quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, bis-hydroxy/methoxy amodimethicones, bis-cetearyl amodimethicone, amodimethicone, bis(C13-15 alkoxy) PG amodimethicones, aminopropyl phenyl trimethicones, aminopropyl dimethicones, bis-amino PEG/PPG-41/3 aminoethyl PG-propyl dimethicones, caprylyl methicones, and a combination thereof, even more preferably amodimethicone;

wherein the dimethicone oil of (d)(i) and the amodimethicone of (d)(ii) are in a weight ratio of about 10:1 to about 1:1, preferably wherein the ratio of (d)(i) to (d)(ii) is about 8:1 to about 2:1, more preferably wherein the ratio of d)(i) to (d)(ii) is about 8:1 to about 3:1;

(e) about 50 to about 92 wt. %, preferably about 60 to about 90 wt. %, more preferably about 70 to about 85 wt. % of water;

(f) about 0.01 to about 15 wt. %, preferably about 0.1 to about 10 wt. %, more preferably about 1 to about 8 wt. % of one or more water-soluble organic solvents, preferably one or more water-soluble organic solvents chosen from glycerin, $C_{1-6}$ mono-alcohols, polyols (polyhydric alcohols), glycols, and a combination thereof, even more preferably one or more water-soluble organic solvents selected from glycerin, $C_{1-6}$ mono-alcohols, and a combination therefore;

(g) optionally, about 0.01 to about 8 wt. %, preferably about 0.05 to about 6 wt. %, more preferably about 0.1 to about 5 wt. % of one or more thickening agents, preferably one or more thickening agents selected from carboxylic acid polymers, crosslinked polyacrylate polymers, polyacrylamide polymers, polysaccharides, gums, modified gums, and a combination thereof, more preferably one or more thickening agents selected from guar gums and modified guar gums, more preferably one or more nonionic guar gums and/or modified guar gums, in particular, hydroxypropyl guar;

(h) about 0.1 to about 6 wt. %, preferably about 0.5 to about 5 wt. %, more preferably about 1 to about 5 wt. %, even more preferably about 2 to about 4 wt. % of one or more C1-C9 non-polymeric and non-thiol, mono-, di-, and/or tri-carboxylic acids, salts thereof, or a combination thereof, preferably one or more C1-C9 non-polymeric and non-thiol, mono-, di-, and/or tricarboxylic acids selected from formic acid, acetic acid, lactic acid, propionic acid, butyric acid, gluconic acid, valeric acid, caproic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, (i) optionally, about 0.01 to about 10 wt. %, more preferably about 0.1 to about 8 wt. %, more preferably about 0.2 to about 6 wt. % of one or more emollients, preferably one or more hydrophobic emollients, more preferably wherein the one or more emollients are selected from waxes, fatty esters, and a combination thereof (for example carnauba wax, beeswax, candelilla wax, paraffin, Japan wax, microcrystalline wax, isopropyl palmitate, isopropyl myristate, myristyl lactate, cetyl esters, isotridecyl isononanoate, C12-15 alkyl benzoate, caprylic/capric triglyceride and pentaerythrityl tetraisostearate, and a combination thereof, in particular cetyl esters;

(j) optionally, about 0.01 to about 10 wt. %, preferably about 0.1 to about 6 wt. %, more preferably about 0.1 to about 4 wt. % of one or more surfactants, preferably wherein one or more surfactants are selected from nonionic surfactants and optionally, an amphoteric surfactants, more preferably wherein the one or more surfactants are nonionic surfactants, preferably wherein at least one of the one or more nonionic surfactants is polyethoxylated and/or polypropoxylated;

(k) optionally, about 0.01 to about 10 wt. %, preferably about 0.1 to about 8 wt. %, more preferably about 1 to about 6 wt. % of one or more miscellaneous ingredients, for example, one or more miscellaneous ingredients selected from preservatives, fragrances, pH adjusters, salts, chelating agents, buffers, antioxidants, flavonoids, vitamins, botanical extracts, UV filtering agents, proteins, protein hydrolysates, and/or isolates, fillers, composition colorants, cationic polymers, and a combination thereof;

wherein all weight percentages are based on a total weight of the hair treatment composition.

Form

The hair treatment compositions of the instant disclosure may be in a variety of different forms. For example, the hair treatment compositions can be a liquid, serum, gel, a paste, or cream. In one embodiment, the hair treatment composition has a viscosity allowing it to be sprayed onto hair using a typical hand-pump spray bottle. In various embodiments, the hair treatment composition is in the form of an emulsion, preferably an oil-in-water emulsion.

pH

The pH of the hair treatment compositions of the instant disclosure will vary. Nonetheless, in various embodiments, the pH of the hair treatment composition is from about 3 to about 10. In further embodiments, the pH of the hair treatment composition is about 3 to about 8, about 3 to about 7, about 3 to less than 7, about 3 to about 6, about 3 to about 5, about 3.5 to about 10, about 3.5 to about 8, about 3.5 to about 6, about 3.5 to about 5, about 4 to about 10, about 4 to about 8, about 4 to about 6, or about 4 to about 5.

Viscosity

The viscosity of the hair treatment compositions will vary. Nonetheless, in various embodiments, the viscosity of the hair treatment compositions is about 100 cps to about 50,000 cps at a temperature of 25° C. In further embodiments, the viscosity of the hair treatment compositions is about 100 to about 40,000 cps, about 100 to about 30,000 cps, about 100 to about 20,000, about 100 to about 15,000 cps, about 500 to about 40,000 cps, about 500 to about 30,000 cps, about 500 to about 20,000 cps, about 500 to about 15,000 cps, about 1,000 to about 30,000 cps, about 1,000 to about 20,000 cps, about 1,000 to about 15,000 cps, about 2,000 to about 50,000 cps, about 2,000 to about 40,000 cps, about 2,000 to about 30,000 cps, about 2,000 to about 20,000 cps, about 2,000 to about 15,000 cps, about 5,000 cps to about 50,000 cps, about 5,000 cps to about 40,000 cps, about 5,000 to about 30,000 cps, about 5,000 to about 20,000 cps, about 5,000 to about 15,000 cps, or about 5,000 to about 12,000 cps at a temperature of 25° C. The viscosity can be measured with a Brookfield DV-LL+ Pro Viscometer using Spindle RV-05 and rotational speed of 10% RPM.

Stability

The hair treatment compositions are stable and homogenous. In other words, the hair treatment compositions do not visually phase separate or develop sedimentation, and do not form visibly observable particulates. For instance, the hair treatment compositions remain stable for at least 1 week at room temperature; the hair treatment compositions remain stable for at least 8 weeks at 4° C.; and/or the hair treatment compositions remain stable for at least 8 weeks at 45° C. In various embodiments, the hair treatment compositions remain visually homogenous and free from visual phase separation and particulate formation for at least 1, 2, 4, and/or 8 weeks at room temperature (25° C.).

Methods

The hair treatment compositions of the instant disclosure are useful in methods for treating hair. The methods include applying a hair treatment composition according to the instant disclosure to the hair and subsequently rinsing the hair treatment composition from the hair, i.e., in a "rinse-off" method. The hair treatment compositions may be used, for example, as a conditioner composition or a conditioning mask that is applied to the hair before or after shampooing the hair; or it can be used as a conditioner composition that used without shampooing the hair. Typically, the hair treatment composition is applied to wet or damp hair, massaged into/throughout the hair, and subsequently rinsed from the hair before optionally drying and/or styling the hair. The hair treatment composition may be allowed to remain on the hair prior to rinsing for a period of time, for example, a period of time of about 10 seconds to about 10 minutes, prior to rinsing from the hair. The hair treatment composition may be allowed to remain on the hair for about 10 seconds to about 5 minutes, about 10 seconds to about 2 minutes, about 30 seconds to about 10 minutes, about 30 seconds to about 5 minutes, about 30 seconds to about 2 minutes, about 1 minute to about 10 minutes, about 1 minute to about 5 minutes, or about 1 minute to 2 about 2 minutes, including any combination, sub-combination, range, or sub-range thereof.

In various embodiments, the hair treatment compositions of the instant disclosure are useful in methods, wherein the hair treatment composition is applied to the hair and not subsequently (e.g., immediately within an hour or less) rinsed from the hair, i.e., in a "leave-on" method. The hair treatment composition may be applied to wet hair, damp hair, or dry hair and allowed to remain on the hair without rinsing, for example, without rinsing before styling and/or setting the hair.

The methods of treating hair, according to the procedures discussed above, are useful for conditioning the hair. The procedures are also useful in methods for improving natural look and feel of the hair, reducing hair frizz, improving hair smoothness, hair alignment, and/or hair shine. The methods also relate to increasing the hydrophobicity of the hair. Thus, the instant disclosure relates to methods for: (a) conditioning the hair; (b) improving the look and feel of hair; (c) reducing hair frizz or propensity for frizzing; (d) improving hair smoothness, (e) improving hair alignment; (e) improving or increasing hair shine; (f) improving moisturization of hair; and/or (g) improve the softness of hair.

Kits

The hair treatment compositions disclosed herein may be provided in a kit. For example, one or more of the hair treatment compositions of the instant disclosure may be included in a kit that also includes one or more additional hair treatment compositions, for example, one or more cleansing compositions, in particular, one or more shampoo compositions. All of the various compositions in the kit are separately contained. In some instances, the kits include one or more hair treatment compositions according to the instant disclosure and one or more shampoo compositions, wherein each of the one or more hair treatment compositions and the one or more shampoo compositions are separately contained.

Example 1

Inventive Compositions

| | | | 1 | 2 |
|---|---|---|---|---|
| (a) | Fatty Alcohol | CETEARYL ALCOHOL | 5.5 | 5.5 |
| (b) | Liquid Alkane | C15-19 ALKANE | 1 | 3 |
| | Ratio (a)/(b) | | 5.5 | 1.8 |
| (c)(i) | Mono-alkyl Cationic | BEHENTRIMONIUM CHLORIDE | 4.3 | 4.3 |
| | Surfactant | CETRIMONIUM CHLORIDE | 0.04 | 0.04 |
| (c)(ii) | Di-alkyl Cationic Surfactant | DICETYLDIMONIUM CHLORIDE | 0.8 | 0.8 |
| | Ratio of ((c)(i)/(c)(ii)) | | 5.4 | 5.4 |
| (d)(i) | Dimethicone Oil | DIMETHICONE | 2.8 | 2.8 |
| (d)(ii) | Amino Silicone | AMODIMETHICONE | 1.7 | 1.7 |
| | Ratio of ((d)(i)/(d)(ii)) | | 1.6 | 1.6 |
| (f) | Water Soluble | GLYCERIN | 1 | 1 |
| | Organic Solvent | ISOPROPYL ALCOHOL | 1.2 | 1.2 |
| (g) | Thickening Agent | HYDROXYPROPYL GUAR | 0.25 | 0.25 |
| (h) | Carboxylic acid/ | CITRIC ACID | 1 | 1 |
| | salt thereof | SODIUM CITRATE | 1.1 | 1.1 |
| (i) | Emollient | CETYL ESTERS | 0.5 | 0.5 |
| (j) | Surfactant | TRICEDETH-6 | 0.1 | 0.1 |
| (k) | Miscellaneous (antioxidants, fragrance, preservatives, chelating agents, etc). | | ≤5 | ≤5 |
| (e) | Water | | QS | QS |
| | pH | | 4.0 | 4.0 |
| | Viscosity | | 8600* | 9500* |

*at 25° C. measured with a Brookfield DV-LL + Pro Viscometer using Spindle RV-05 and rotational speed of 10% RPM.

Example 2

Inventive & Comparative Compositions

| | | | Inventive | | Comparative | | | | |
|---|---|---|---|---|---|---|---|---|---|
| | | | 1 | 2 | 1 | 2 | 3 | 4 | 5 |
| (a) | Fatty Alcohol | CETEARYL ALCOHOL | 5.5 | 5.5 | 0 | 5.5 | 5.5 | 5.5 | 5.5 |
| (b) | Liquid Alkane | C16-19 ALKANE | 1 | 0.3 | 1 | 0 | 1 | 1 | 1 |
| | Ratio of (a)/(b) | | 5.5 | 18.3 | NA | NA | 5.5 | 5.5 | 5.5 |
| (c)(i) | Mono-alkyl Cationic | BEHENTRIMONIUM CHLORIDE | 4.3 | 4.3 | 4.3 | 4.3 | 4.3 | 0 | 43 |
| | Surfactant | CETRIMONIUM CHLORIDE | 0.04 | 0.04 | 0.04 | 0.04 | 0.04 | 0.04 | 0.04 |
| (c)(ii) | Di-alkyl Cationic Surfactant | DICETYLDIMONIUM CHLORIDE | 0.8 | 0.8 | 0.8 | 0.8 | 0 | 0.8 | 0.8 |
| | Ratio of (c)(i)/(c)(ii) | | 5.4 | 5.4 | 5.4 | 5.4 | NA | 0.05 | 5.4 |
| (d)(i) | Dimethicone | DIMETHICONE | 2.8 | 2.8 | 2.8 | 2.8 | 2.8 | 2.8 | 0.4 |
| (d)(ii) | Amino-Silicone | AMODIMETHICONE | 1.7 | 1.7 | 1.7 | 1.7 | 1.7 | 1.7 | 1.1 |
| | Ratio of (d)(i)/(d)(ii) | | 1.6 | 1.6 | 1.6 | 1.6 | 1.6 | 1.6 | 0.36 |
| (f) | Water Soluble | GLYCERIN | 1 | 1 | 1 | 1 | 1 | 1 | 1 |
| | Organic Solvent | ISOPROPYL ALCOHOL | 1.2 | 1.2 | 1.2 | 1.2 | 1.2 | 1.2 | 1.2 |
| (g) | Thickening Agent | HYDROXYPROPYL GUAR | 0.3 | 0.3 | 0.3 | 0.3 | 0.3 | 0.3 | 0.3 |
| (h) | Carboxylic | CITRIC ACID | 1 | 1 | 1 | 1 | 1 | 1 | 1 |
| | acid/salt | SODIUM CITRATE | 1.1 | 1.1 | 1.1 | 1.1 | 1.1 | 1.1 | 1.1 |
| (i) | Emollient | CETYL ESTERS | 0.5 | 0.5 | 0.5 | 0.5 | 0.5 | 0.5 | 0.5 |
| (l) | Surfactant | TRIDECETH-6 | 0.1 | 0.1 | 0.1 | 0.3 | 0.1 | 0.1 | 0.1 |
| (k) | Miscellaneous | | ≤5 | ≤5 | ≤5 | ≤5 | ≤5 | ≤5 | ≤5 |
| (e) | WATER | | QS | QS | QS | QS | QS | QS | QS |

| | | | Comparative | | | | |
|---|---|---|---|---|---|---|---|
| | | | 6 | 7 | 8 | 9 | 10 |
| (a) | Fatty Alcohol | CETEARYL ALCOHOL | 5.5 | 5.5 | 0.3 | 5.5 | 5.5 |
| (b) | Liquid Alkane | C16-19 ALKANE | 1 | 1 | 5.5 | 1 | 1 |
| | Ratio of (a)/(b) | | 5.5 | 5.5 | 0.1 | 5.5 | 5.5 |
| (c)(i) | Mono-alkyl Cationic | BEHENTRIMONIUM CHLORIDE | 4.3 | 4.3 | 4.3 | 4.3 | 0.9 |
| | Surfactant | CETRIMONIUM | | | 0.04 | 0.04 | 0.04 |

-continued

| | | | | | | | |
|---|---|---|---|---|---|---|---|
| | | CHLORIDE | | | | | |
| (c)(ii) | Di-alkyl Cationic Surfactant | DICETYLDIMONIUM CHLORIDE | 0.8 | 0.8 | 0.8 | 0.2 | 4 |
| | Ratio of (c)(i)/(c)(ii) | | 5.4 | 5.4 | 5.4 | 21.7 | 0.24 |
| (d)(i) | Dimethicone | DIMETHICONE | 2.8 | 0.4 | 2.8 | 2.8 | 2.8 |
| (d)(ii) | Amino-Silicone | AMODIMETHICONE | 0.6 | | 1.7 | 1.7 | 1.7 |
| | Ratio of (d)(i)/(d)(ii) | | 4.67 | NA | 1.6 | 1.6 | 1.6 |
| (f) | Water Soluble Organic Solvent | GLYCERIN | 1 | 1 | 1 | 1 | 1 |
| | | ISOPROPYL ALCOHOL | 1.2 | 1.2 | 1.2 | 1.2 | 1.2 |
| (g) | Thickening Agent | HYDROXYPROPYL GUAR | 0.3 | 0.3 | 0.3 | 0.3 | 0.3 |
| (h) | Carboxylic acid/salt | CITRIC ACID | 1 | 1 | 1 | 1 | 1 |
| | | SODIUM CITRATE | 1.1 | 1.1 | 1.1 | 1.1 | 1.1 |
| (i) | Emollient | CETYL ESTERS | 0.5 | 0.5 | 0.5 | 0.5 | 0.5 |
| (l) | Surfactant | TRIDECETH-6 | | | 0.1 | 0.1 | 0.1 |
| (k) | Miscellaneous | | ≤5 | ≤5 | ≤5 | ≤5 | ≤5 |
| (e) | WATER | | QS | QS | QS | QS | QS |

Example 3

Testing

The sensorial properties of hair swatches treated with the compositions set forth in Example 2 were assessed by two different experts. Inventive Composition 1 was used as a benchmark to compare all additional compositions. Highly bleached Caucasian hair swatches (SA40, 2.7 g, 27 cm) were used. Each hair swatch was cleansed with a standard shampoo. After rinsing the shampoo from the swatches, the swatches were treated with a composition from Example 2. After thoroughly massaging the composition into the hair swatch, the composition was rinsed away. Excess water was removed from the hair swatches with a towel and sensorial properties of the wet hair were evaluated. The hair swatches were then blow dried and again sensorial properties were evaluated. The results are presented in the table below.

| Sensorial Property on hair swatch | | | | | | | | | | | | |
|---|---|---|---|---|---|---|---|---|---|---|---|---|
| | Inventive | | Comparative | | | | | | | | | |
| | 1 | 2 | 1 | 2 | 3 | 4 | 5 | 6 | 7 | 8 | 9 | 10 |
| Smoothness on rinsing | BENCHMARK | = | -- | = | NOT STABLE | + | - | - | -- | -- | = | -- |
| Combing on wet | | = | -- | - | | - | -- | - | - | -- | - | -- |
| Smoothness on wet | | = | -- | - | | = | = | = | = | -- | = | -- |
| Combing on dry | | = | - | = | | - | -- | -- | -- | - | + | -- |
| Smoothness on dry | | + | = | - | | = | - | - | - | = | = | - |
| Alignment on dry | | = | - | = | | = | - | - | - | = | = | -- |
| End seal on dry | | = | = | - | | -- | -- | -- | -- | - | = | - |

++ Superior to Benchmark
+ Somewhat Superior to Benchmark
= Same as the Benchmark
– Somewhat Inferior to Benchmark
–– Inferior to Benchmark Inventive Compositions 1 and 2 outperformed the comparative compositions by providing a myriad of desirable sensorial attributes to the hair. Comparative Composition 3 was not stable upon preparation and therefore could not be tested. The data show that including the claimed components in the claimed amounts and ratios results in a hair treatment composition that imparts multiple desirable attributes to the hair, for example, smoothness, ease of combing, alignment, and end seal.

Definitions

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular. Thus, the term "a mixture thereof" is interchangeable with "mixtures thereof." Throughout the disclosure, the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements chosen from A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Some of the various categories of components identified may overlap. In such cases where overlap may exist and the composition/product includes two overlapping components (or more than two overlapping components), an overlapping component does not represent more than one component. For example, a component such as a fatty ester may fall within a definition of a "emollient" and within a definition of an "nonionic surfactant." If a particular composition/product requires both an emollient and a nonionic surfactant, a single fatty ester can serve as the emollient or the nonionic surfactant (a single fatty ester cannot serve as both the emollient and the nonionic surfactant).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

Other than in the operating examples, or where otherwise indicated, all numbers expressing quantities of ingredients and/or reaction conditions are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

In the context of the instant disclosure, a "composition colorant" is a compound that colors the composition but does not have an appreciable coloring effect on hair. In other words, the composition colorant is included to provide a coloring to the composition for aesthetic appeal, which is not intended to impart coloring properties to hair. Styling gels, for example, can be found in a variety of different colors (e.g., light blue, light pink, etc.) yet application of the styling gel to the hair does not change the color of the hair.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention). Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. The term "substantially free" or "essentially free" as used herein may also mean that the specific material is not added to the composition but may still be present in a raw material that is included in the composition.

Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair treatment composition comprising:

(a) about 1 to about 15 wt. % of one or more fatty alcohols;

(b) about 0.5 wt. % to about 10 wt. % one or more liquid alkane oils having a carbon chain length of C11 to C20;
  wherein the one or more fatty alcohols of (a) and the one or more liquid alkane oils of (b) are in a weight ratio of about 10:1 to about 2:1 ((a):(b));

(c) about 1 to about 10 wt. % of a combination of cationic surfactants comprising:
  (c)(i) about 0.5 to about 10 wt. % of one or more mono-alkyl cationic surfactants; and
  (c)(ii) about 0.1 to about 6 wt. % of one or more di-alkyl cationic surfactants;
  wherein the one or more mono-alkyl cationic surfactants of (c)(i) and the one or more di-alkyl cationic surfactants of (c)(ii) are in a weight ratio of about 10:1 to about 1:1 ((c)(i):(c)(ii));

(d) about 1 to about 10 wt. % of a combination of silicone oils comprising:
  (d)(i) about 0.5 to about 20 wt. %, of one or more non-volatile dimethicone oils; and
  (d)(ii) about 0.1 to about 15 wt. % of one or more non-piperidinyl amino silicone oils; wherein the one or more non-volatile dimethicone oils of (d)(i) and the one or more non-piperidinyl amino silicone oils of (d)(ii) are in a weight ratio of about 1:1 to about 8:1; and (e) about 50 to about 92 wt. % of water;

wherein all weight percentages are based on a total weight of the hair treatment composition; and whereby the weight ratio of the one or more fatty alcohols of (a) and the one or more liquid alkane oils of (b) is such that the hair treatment composition exhibits improved wet combing compared to a hair treatment composition outside the weight ratio (a):(b).

2. The hair treatment composition of claim 1, wherein the one or more fatty alcohols of (a) are selected from cetearyl alcohol, decyl alcohol, undecyl alcohol, dodecyl alcohol, myristyl alcohol, cetyl alcohol, stearyl alcohol, isostearyl alcohol, isocetyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, octyldodecanol, 2-octyl-1-dodecanol, and a mixture thereof.

3. The hair treatment composition of claim 1, wherein the liquid alkanes having a carbon chain length of C11 to C20 are selected from isohexadecane, C15-19 alkane, isododecane, undecane, tridecane, and a combination thereof.

4. The hair treatment composition of claim 1, wherein the one or more mono-alkyl cationic surfactants of (c)(i) are selected from mono-alkyl trimonium halide compounds.

5. The hair treatment composition of claim 1, wherein the one or more di-alkyl cationic surfactants of (c)(ii) are selected from di-alkyl dimonium halide compounds.

6. The hair treatment composition of claim 1, wherein the combination of cationic surfactants of (c) comprises:

(c)(i) about 2 to about 8 wt. % of the one or more mono-alkyl cationic surfactants; and (c)(ii) about 0.2 to about 2 wt. % of the one or more di-alkyl cationic surfactants.

7. The hair treatment composition of claim 1, wherein the one or more non-volatile dimethicone oils of (d)(i) and the one or more non-piperidinyl amino silicone oils of (d)(ii) are in a weight ratio of about 3:1 to about 8:1.

8. The hair treatment composition of claim 1, wherein the one or more non-piperidinyl amino silicone oils are selected from amodimethicone, aminopropyl dimethicone, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-17, silicone quaternium-18, silicone quaternium-20, silicone quaternium-21, silicone quaternium-22, quaternium-80, silicone quaternium-2 panthenol succinate, silicone quaternium-16/glycidyl dimethicone crosspolymer, and a combination thereof.

9. The hair treatment composition of claim 8, wherein the one or more non-piperidinyl amino silicone oils include amodimethicone or aminopropyl dimethicone or mixture thereof.

10. The hair treatment composition of claim 1, further comprising:

(f) about 0.01 to about 15 wt. % of one or more water soluble organic solvents.

11. The hair treatment composition of claim 10, wherein the one or more water soluble organic solvents are selected from glycerin, C2-C6 mono-alcohols, polyols (polyhydric alcohols), glycols, and a mixture thereof.

12. The hair treatment composition of claim 1, further comprising:

(g) about 0.01 to about 8 wt. % of one or more thickening agents.

13. The hair treatment composition of claim 12, wherein the one or more thickening agents are selected from polyacrylate crosspolymers, cationic acrylate copolymers, anionic acrylic or carboxylic acid polymers, polyacrylamide polymers, polysaccharides, gums, polyquaterniums, vinylpyrrolidone homopolymers/copolymers, C8-24 hydroxyl substituted aliphatic acid, C8-24 conjugated aliphatic acid, sugar fatty esters, polyglyceryl esters, and a combination thereof.

14. The hair treatment composition of claim 1, further comprising:

(h) about 0.1 to about 6 wt. % of one or more C1-C9 non-polymeric and non-thiol, mono-, di-, and/or tri-carboxylic acids, salts thereof, or a combination thereof.

15. The hair treatment composition of claim 14, wherein the one or more one or more C1-C9 non-polymeric and non-thiol, mono-, di-, and/or tri-carboxylic acids are selected from formic acid, acetic acid, lactic acid, propionic acid, butyric acid, gluconic acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, and arachidic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, and 2,6-naphthalene dicarboxylic acid, citric acid, isocitric acid, aconitric acid, propane-1,2,3-tricarboxylic acid, and benzene-1,3,5-tricarboxylic acid, a salt thereof, and a combination thereof.

16. The hair treatment composition of claim 1, further comprising:

(i) about 0.01 to about 10 wt. % of one or more emollients.

17. A hair treatment composition comprising:

(a) about 1 to about 15 wt. % of one or more fatty alcohols;

(b) about 0.5 wt. % to about 10 wt. % of one or more liquid alkane oils having a carbon chain length of C11 to C20;

wherein the one or more fatty alcohols of (a) and the one or more liquid alkane oils of (b) are in a weight ratio of about 20:1 to about 1:1;

(c) about 1 to about 10 wt. % of a combination of cationic surfactants comprising:

(c)(i) about 1 to about 6 wt. % of behentrimonium chloride, cetrimonium chloride, or mixtures thereof; and (c)(ii) about 0.1 to about 4 wt. % of dicetyldimonium chloride;

wherein the behentrimonium chloride, cetrimonium chloride, or mixtures thereof of (c)(i) and the dicetyldimonium chloride of (c)(ii) are in a weight ratio of about 10:1 to about 1:1 ((c)(i):(c)(ii));

(d) about 1 to about 10 wt. % of a combination of silicone oils comprising:

(d)(i) about 1 to about 10 wt. % of dimethicone oil; and (d)(ii) about 0.5 to about 5 wt. % amodimethicone;

wherein the dimethicone oil of (d)(i) and the amodimethicone of (d)(ii) are in a weight ratio of about 1:1 to about 8:1;

(e) about 60 to about 85 wt. % of water;

(f) one or more water soluble organic solvents;

(g) optionally, one or more thickening agents;

(h) about 0.5 to about 5 wt. % of one or more C1-C9 non-polymeric and non-thiol, mono-, di-, and/or tri-carboxylic acids, salts thereof, or a combination thereof;

(i) optionally, one or more emollients;

(j) optionally, one or more surfactants; and (k) optionally, one or more miscellaneous ingredients;

wherein all weight percentages are based on a total weight of the hair treatment composition; and whereby the weight ratio of the one or more fatty alcohols of (a) and the one or more liquid alkane oils of (b) is such that the hair treatment composition exhibits improved wet combing compared to a hair treatment composition outside the weight ratio (a):(b).

18. A method for treating hair comprising applying the hair treatment composition of claim 1 to the hair.

19. The method of claim 18, wherein the hair treatment composition is a rinse-off composition and is rinsed from the hair before drying and styling the hair.

20. The hair treatment composition according to claim 17, wherein the one or more liquid alkane oils are selected from isohexadecane, C15-19 alkane, isododecane, undecane, tridecane, and a combination thereof.

21. The hair treatment composition according to claim 1, wherein the one or more fatty alcohols of (a) and the one or more liquid alkane oils of (b) are in a weight ratio of about 10:1 to about 5.5:1 ((a):(b)).

22. The hair treatment composition according to claim 1, wherein the one or more fatty alcohols of (a) and the one or more liquid alkane oils of (b) are in a weight ratio of about 6:1 to about 2:1 ((a):(b)).

23. A hair treatment composition comprising:

(a) about 1 to about 15 wt. % of one or more fatty alcohols;

(b) about 0.5 wt. % to about 10 wt. % of one or more liquid alkane oils having a carbon chain length of C11 to C20;

wherein the one or more fatty alcohols of (a) and the one or more liquid alkane oils of (b) are in a weight ratio of about 20:1 to about 1:1;

(c) about 1 to about 10 wt. % of a combination of cationic surfactants comprising:

(c)(i) about 1 to about 6 wt. % of behentrimonium chloride, cetrimonium chloride, or mixtures thereof; and (c)(ii) about 0.1 to about 4 wt. % of dicetyldimonium chloride;

wherein the behentrimonium chloride, cetrimonium chloride, or mixtures thereof of (c)(i) and the dicetyldimonium chloride of (c)(ii) are in a weight ratio of about 10:1 to about 1:1 ((c)(i):(c)(ii));

(d) about 1 to about 10 wt. % of a combination of silicone oils comprising:

(d)(i) about 1 to about 10 wt. % of dimethicone oil; and (d)(ii) about 0.5 to about 5 wt. % amodimethicone;

wherein the dimethicone oil of (d)(i) and the amodimethicone of (d)(ii) are in a weight ratio of about 1:1 to about 8:1;

(e) about 60 to about 85 wt. % of water;

(f) about 0.01 to about 15 wt. % of one or more water soluble organic solvents;

(g) optionally, about 0.01 to about 8 wt. % of one or more thickening agents;

(h) about 0.5 to about 5 wt. % of one or more C1-C9 non-polymeric and non-thiol, mono-, di-, and/or tri-carboxylic acids, salts thereof, or a combination thereof;

(i) optionally, about 0.01 to about 10 wt. % of one or more emollients;

(j) optionally, about 0.01 to about 10 wt. % of one or more surfactants; and (k) optionally, about 0.01 to about 10 wt. % of one or more miscellaneous ingredients;

wherein all weight percentages are based on a total weight of the hair treatment composition; and whereby the weight ratio of the one or more fatty alcohols of (a) and the one or more liquid alkane oils of (b) is such that the hair treatment composition exhibits improved wet combing compared to a hair treatment composition outside the weight ratio (a):(b).

* * * * *